United States Patent [19]

Norman et al.

[11] Patent Number: 5,098,516
[45] Date of Patent: Mar. 24, 1992

[54] PROCESSES FOR THE CHEMICAL VAPOR DEPOSITION OF COPPER AND ETCHING OF COPPER

[75] Inventors: John A. T. Norman, Whitehall; Paul N. Dyer, Allentown, both of Pa.

[73] Assignee: Air Products and Chemicals, Inc., Allentown, Pa.

[21] Appl. No.: 636,316

[22] Filed: Dec. 31, 1990

[51] Int. Cl.$^5$ .................. C23C 16/18; C23F 1/12
[52] U.S. Cl. .................. 156/666; 156/646; 156/654; 156/655; 156/656; 156/664; 427/250; 427/252; 427/253; 427/255.4
[58] Field of Search .......... 427/250, 252, 253, 255.4; 156/646, 654, 655, 656, 664, 666

[56] References Cited

U.S. PATENT DOCUMENTS

| | | | |
|---|---|---|---|
| 3,356,527 | 12/1967 | Moshier et al. | 117/107.2 |
| 3,594,216 | 7/1971 | Charles et al. | 427/252 |
| 4,321,073 | 3/1982 | Blair | 427/252 |
| 4,425,281 | 1/1984 | Doyle | 260/430 |
| 4,622,095 | 11/1986 | Grobman et al. | 156/656 |
| 4,904,340 | 2/1990 | Miracky et al. | 156/656 |
| 4,948,623 | 8/1990 | Beach et al. | 427/252 |

FOREIGN PATENT DOCUMENTS 2823068 12/1978 Fed. Rep. of Germany ...... 156/666

OTHER PUBLICATIONS

T. Ohba et al., "Tungsten and Other Advanced Metals for VLSI/ULSI Applications V"; Ed. by S. S. Wong, S. Furukawa; MRS, Pittsburgh, Pa.; p. 273; (1990).
T. Ohba et al.; *Tech. Dig.;* IEDM, p. 213 (1987).
R. L. Van Hemert et al.; *J. Electrochem. Soc.;* (112); 1123 (1965).
Reisman et al.; *J. Electrochemical Soc.;* vol. 136; No. 11; Nov. 1989.
A. E. Kaloyeros et al.; *Journal of Electronic Materials;* vol. 19; No. 3; 271; (1990).
C. Oehr et al.; *Appl. Phy. A.;* (45); 151-154; (1988).
F. A. Houle et al.; *J. Val. Sci. Technol.* A 4 2452-2458; (1986).
F. A. Houle et al.; *Appl. Phys. Letter* (46); 204-206 (1985).
G. S. Girolami et al.; *Chem. Mater.* (1); 8-10; (1989).
Beach et al.; *Chem. Mater.* (2); 216-219; (1990).

*Primary Examiner*—Shrive Beck
*Assistant Examiner*—Margaret Burke
*Attorney, Agent, or Firm*—Mark L. Rodgers; William F. Marsh; James C. Simmons

[57] ABSTRACT

A process is provided for selectively depositing copper films on metallic or other electrically conducting portions of substrate surfaces by contacting the substrate at a temperature from 110° to 190° C. with a volatile organometallic copper complex, in the gas phase, represented by the structural formula:

$$Cu^{+1}(R^1-\overset{O}{\underset{\|}{C}}-\overset{R^2}{\underset{|}{C}}-\overset{O}{\underset{\|}{C}}-R^3)^{-1} \cdot L$$

wherein $R^1$ and $R^3$ are each independently $C_1$-$C_8$ perfluoroalkyl, $R^2$ is H or $C_1$-$C_8$ perfluoroalkyl and L is carbon monoxide, an isonitrile, or an unsaturated hydrocarbon ligand containing at least one non-aromatic unsaturation.

12 Claims, 1 Drawing Sheet

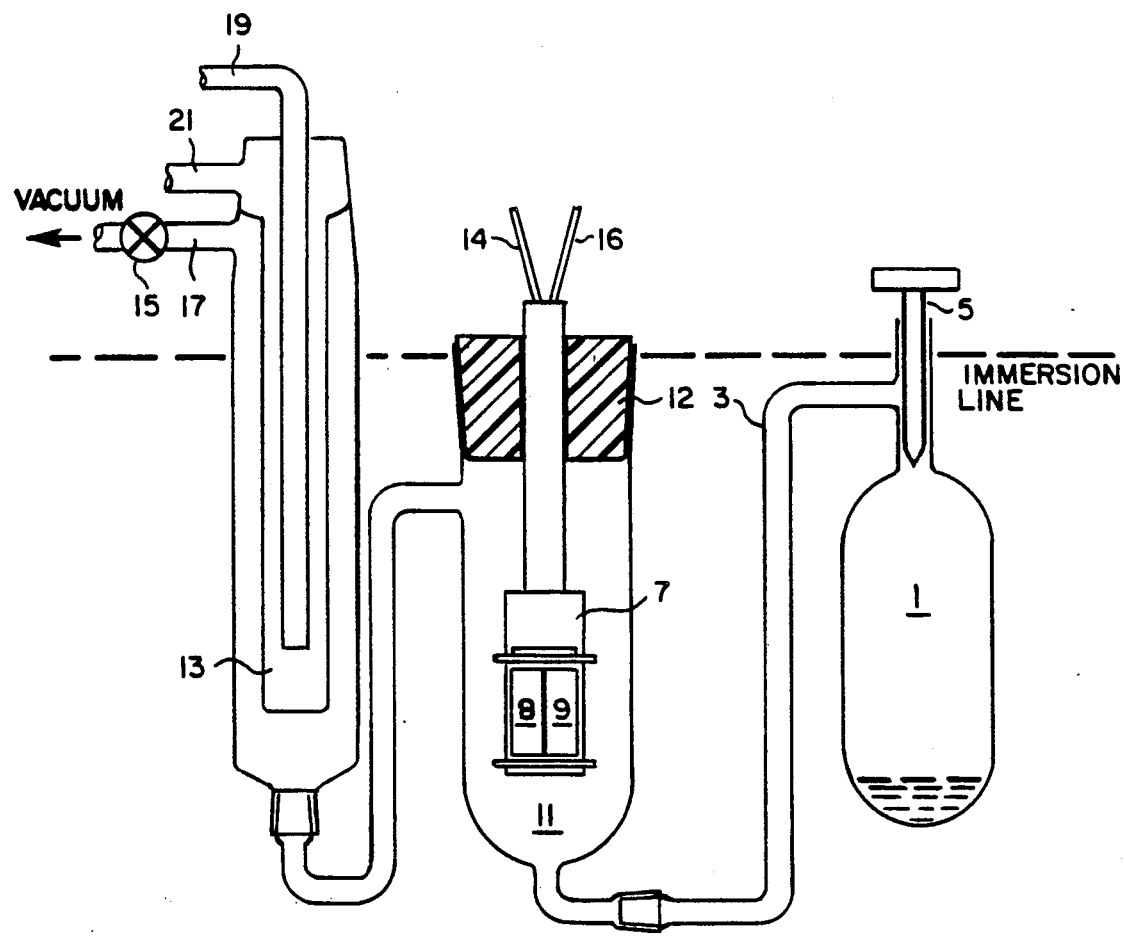

PROCESSES FOR THE CHEMICAL VAPOR DEPOSITION OF COPPER AND ETCHING OF COPPER

TECHNICAL FIELD OF THE INVENTION

The present invention relates to the deposition of copper films onto conducting metallic or metallic-like surfaces.

BACKGROUND OF THE INVENTION

In the electronics industry there is a steady trend towards manufacturing microprocessors of increasingly high speed and large information storage capacity. This requires the individual electrical devices such as transistors, etc. within the microprocessors to be fabricated at an increasingly small scale. The metallic electrical interconnects between the devices also need to be miniaturized. As device and interconnect dimensions approach one-half to one-quarter of a micron, the choice of interconnect metal becomes critical. The large current densities resulting from small interconnect cross sectional areas can lead to major problems such as electromigration, stress migration, and voiding where the metal lines become fractured or otherwise physically degraded under operating conditions, a major drawback with aluminum alloys. Metal interconnects also need to provide the lowest electrical resistance path possible since resistance-capacitance delays become a dominant factor in circuit performance at sub half micron levels. The aluminum that is widely used in present day interconnect manufacturing is reasonably conductive (2.7 microohm cm), but needs to be alloyed with 0.5 to 4.0% Cu to minimize the electromigration tendencies of the pure metal. Tungsten, also widely used, is electromigration resistant but is of higher resistivity (5.4 microohm cm). Considering these facts, copper should be an excellent interconnect metal as it is both highly conductive (1.7 microohm cm) and electromigration resistant.

Metallic interconnects are typically horizontal lines (runners) or plugs (vias) that wire together devices in microprocessors. At feature sizes of >1 micron these metallic components can be built into the microcircuits by PVD (Physical Vapor Deposition) techniques such as sputtering or evaporation. In essence PVD consists of condensing a metal vapor onto a surface or into a hole or channel of a circuit where an electrical connection needs to be formed. Since this is a non-selective metallization, either a postdeposition clean-up (i.e. etch-back) or a predeposition masking of the substrate (i.e. the lift-off technique) is required in order to prepare individual discreet metal components. However, the severe surface topographies presented by sub-micron features preclude the effective use of PVD since this "line of sight" technique cannot provide a uniform conformal coating on such high aspect ratio highly convoluted surfaces. Specific examples of these shortcomings include the phenomena of geometrical shadowing and poor step coverage.

A superior process for producing these microscopic metal features is CVD (Chemical Vapor Deposition). In this technique a volatile metal-organic compound in the gas phase is contacted with areas of a circuit where growth of a metal film (i.e. interconnect) is required. A surface catalyzed chemical reaction then occurs which leads to deposition of the desired metal. Since this is a chemical reaction, there is potential for it to provide surface selective metallization. That is, CVD metal deposition can be made to occur at only specific locations compared to the non-selective PVD processes. Also, since the metal film steadily grows on the desired surface it is of a uniform thickness and highly conformal even to severe geometries. In this respect CVD is naturally suited to fabricating submicron high aspect ratio features.

An example of selective CVD metallization that is currently commercially practiced is the deposition of tungsten onto a silicon surface using tungsten hexafluoride as the volatile organometallic precursor (see T. Ohba, et al., "Tungsten and Other Advanced Metals for VLSI/ULSI Applications V," Ed. by S. S. Wong and S. Furukawa, MRS, Pittsburgh, Pa., 273 (1990)). The chemistry that drives this process can be divided into two steps. Initially the $WF_6$ reacts with the elemental silicon surface to yield tungsten metal and volatile silicon hexafluoride. Hydrogen gas is then added to the system which reduces further $WF_6$ at the freshly formed metal surface thereby yielding additional tungsten and HF gas. Although this system currently enjoys widespread use as the only "selective" CVD metallization process that is widely commercially available, loss of selectivity can be observed and is commonly ascribed to the corrosive nature of HF. T. Ohba, et al., Tech. Dig. IEDM, 213 (1987) teach the use of silane as a reducing agent for $WF_6$ to achieve higher deposition rates while avoiding the production of HF gas.

Desirable selectivities for a copper CVD process include deposition onto conducting metallic or metallic like surfaces such as tungsten, tantalum or titanium nitride versus insulating surfaces such as silicon oxide. These metallic surfaces provide a diffusion barrier between the CVD copper and the underlying silicon substrate that the device is grown upon.

Copper films have previously been prepared via CVD using various copper precursors. Most of these compounds will only deposit copper metal at temperatures higher than 200° C. with no significant selectivity between substrates such as diffusion barrier surfaces vs. silicon oxide. The best known and most frequently used CVD copper precursor is copper$^{+2}$ bis(hexafluoroacetylacetonate). This highly fluorinated organometallic precursor is significantly more volatile than its parent unfluorinated complex copper$^{+2}$ bis(acetylacetonate) and its ease of vaporization readily lends this compound towards CVD processes. The use of this compound as a general precursor for CVD copper metallization was first described by R. L. Van Hemert et al. *J. Electrochem. Soc.* (112), 1123 (1965) and by R. H. Moshier et al. U.S. Pat. No. 3,356,527. More recently Reisman, et al., *J. Electrochemical Soc.*, Vol. 136, No. 11, November 1989 and A. E. Kaloyeros et al., *Journal of Electronic Materials*. Vol. 19, No. 3, 271 (1990) in two independent studies have also evaluated the use of this compound as a copper precursor for electronics applications. In these studies copper films were formed by contacting vapors of copper$^{+2}$(hfac)$_2$, mixed with either an inert gas (argon) or with hydrogen and contacting the mixture with a heated substrate surface. In the case of using hydrogen the copper$^{+2}$ atom in the precursor complex is formally reduced to copper metal while the hfac$^{-1}$ ligand becomes protonated to yield a neutral volatile compound. In the case of using an inert gas the copper$^{+2}$(hfac)$_2$ is simply pyrolyzed to give copper metal and fragments of the hfac ligand.

Pure copper is reported for the hydrogen reduction but oxygen and carbon are found in the films obtained by pyrolysis. However, the lowest deposition temperatures for either process is 250° C. and no strong selectivities towards metallic vs. silicon oxide surfaces are reported. Copper films have also been prepared from copper$^{+2}$(hfac)$_2$ by plasma enhanced deposition, C. Oehr, H. Suhr, Appl. Phy. A. (45) 151-154 (1988), laser photothermal decomposition, F. A. Houle., C. R. Jones., T. Baum., C. Pico., C. A. Korae; *Appl. Phys. Lett.* (46) 204-206 (1985), and photochemical decomposition of copper$^{+2}$(hfac)$_2$ ethanol adducts, F. A. Houle., R. J. Hilson; T. H. Baum., *J. Vac. Sci. Technol. A* (4), 2452-2458 (1986). Some of these methods yield fluorine contaminated films and none are reported to yield selective depositions. Similar hydrogen reduction of volatile copper compounds has also been demonstrated by Charles et al. U.S. Pat. No. 3,594,216 using copper$^{+2}$ β-ketoimine complexes at 400° C. to deposit copper metal films onto glass or quartz substrates. No mention of selectivity is made. G. S. Girolami, et al., *Chem. Mater.* (1) 8-10 (1989) reported using copper$^{+1}$ t-butoxide to yield copper films by CVD at 400° C., but the resultant films were impure in that they contained 5% oxygen.

The only CVD precursors known to deposit pure copper metal films below 200° C. are the copper$^{+1}$ cyclopentadienyl phosphine compounds described by Beech et al., *Chem. Mater.* (2) 216-219 (1990), but these are also not reported to be strongly selective towards metallic or metallic like surfaces vs. silicon oxide or similar insulating dielectrics. An additional problem that this particular class of compounds faces for electronics applications is their potential to contaminate microcircuits with phosphorus, an element that is extensively used as a silicon dopant.

SUMMARY OF THE INVENTION

The present invention is an improved chemical vapor deposition process for selectively depositing pure, thin copper films on metallic or other electrically conducting portions of a substrate surface. The improvement comprises contacting the substrate with a volatile organometallic copper complex having a vapor pressure greater than or equal to 0.01 mm Hg at 100° C. represented by the structural formula:

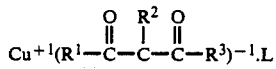

where R$^1$ and R$^3$ are each independently C$_1$-C$_8$ perfluoroalkyl, R$^2$ is H or C$_1$-C$_8$ perfluoroalkyl and L is carbon monoxide, an isonitrile, or an unsaturated hydrocarbon ligand containing at least one non-aromatic unsaturation.

This process provides for the selective deposition of pure copper films onto the metallic or other electrically conducting portions of a substrate surface at low deposition temperatures., i.e. from about 110° to 190° C.

Additionally, it has been found that the deposition reaction can be reversed to cleanly and selectively etch deposited copper from a substrate surface. In this process, a substrate on which has been deposited a copper film is contacted with an organometallic copper complex and an olefin, in the gas phase, represented by the structural formulae.

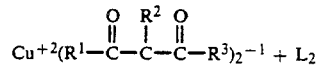

where R$^1$. R$^2$, R$^3$ and L are the same as above.

BRIEF DESCRIPTION OF THE DRAWINGS

The single FIGURE is a diagram of a conventional CVD apparatus used to carry out the process of the present invention.

DETAILED DESCRIPTION OF THE INVENTION

An improved chemical vapor deposition process has been developed for selectively depositing pure, thin copper films on metallic or other electrically conducting portions of a substrate surface. The improvement comprises contacting the substrate with a volatile organometallic copper complex having a vapor pressure greater than or equal to 0.01 mm Hg at 100° C. The copper complexes which are suitable for this deposition application can be represented by the structural formula:

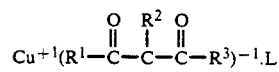

where R$^1$ and R$^3$ are each independently C$_1$-C$_8$ perfluoroalkyl, R$^2$ is H or C$_1$-C$_8$ perfluoroalkyl and L is carbon monoxide, an isonitrile, or an unsaturated hydrocarbon ligand containing at least one non-aromatic unsaturation. In instances wherein L is an unsaturated hydrocarbon ligand, suitable examples include: ethylene, acetylene, 1-octene, isobutylene, 1,5-cyclooctadiene, stilbene, diphenylacetylene, styrene, cyclooctene, 1,5,9-cyclododecatriene, 1.3-hexadiene, isopropylacetylene, 1-decene, 2,5-bicycloheptadiene, 1-octadecene, cyclopentene, octalin, methylene cyclohexane, diphenyl fulvene, 1-octadecyne, benzyl cinnamate, benzal acetophenone, acrylonitrile, maleic anhydride, oleic acid, linolenic acid, acrylic acid, methyl methacrylate and diethyl maleate. Suitable isonitriles include methyl isocyanide, butyl isocyanide, cyclohexyl isocyanide, phenylethyl isocyanide and phenyl isocyanide.

These compounds were originally disclosed in U.S. Pat. No. 4,425,281 for use as complexing agents in a system of processes that separate carbon monoxide, alkenes or alkynes from various gas mixtures. Unexpectedly, we have found these compounds to be volatile compounds which, in their vapor form, can be used under certain conditions to selectively deposit copper metal films of high purity onto either metallic or other electrically conducting surfaces to the exclusion of deposition onto silicon oxide or other similar non-conducting (ie. insulating) surfaces. Such metallic or other electrically conducting surfaces include: W, TiN, Ta, Al, and the like. The deposition conditions are those typically employed in conventional copper CVD applications, with the exception that the present process allows for substantially lower deposition temperatures to be used, i.e., temperatures from about 110° to 190° C., and preferably from 130° to 180° C. While not intending to be bound by theory, the metallization process of the present invention is believed to occur via the following sequence of events:

a). Adsorbtion of the copper$^{+1}$-olefin complex onto the surface(s) to be metallized b). surface catalyzed loss of olefin to yield an unstable copper$^{+1}$ species c). disproportionation of the unstable copper$^{+1}$ species to yield copper metal and a volatile copper$^{+2}$ species This reaction mechanism is represented below for the complex copper$^{+1}$(hfac)·COD where (s) indicates adsorbtion onto the surface and (g) indicates the compound in the gas phase (hfac being an abbreviation for the hexafluoroacetylacetonate anion and COD being an abbreviation for 1,5-cyclooctadiene). Both the COD and the Cu$^{+2}$(hfac)$_2$ are volatile byproducts.

$$2Cu^{+1}(hfac)\cdot COD(g) \rightarrow 2Cu^{+1}(hfac)\cdot COD(s) \quad (1)$$

$$2Cu^{+1}(hfac)\cdot COD(s) \rightarrow 2Cu^{+1}(hfac)(s) + 2COD(g) \quad (2)$$

$$2Cu^{+1}(hfac)(s) \rightarrow Cu^*(s) + Cu^{+2}(hfac)_2(g) \quad (3)$$

The above described mechanism is unique in the field of CVD copper metallization and offers a number of processing advantages. Stabilization of the +1 oxidation state of copper is provided by coordination of an olefin and decomposition to copper metal is caused by loss of an olefin. Therefore, it is possible to control the copper deposition temperature, the rate of deposition and the resulting film morphology by increasing the concentration (i.e. pressure) of the olefin in the system or by adding different olefins. Similarly, normally unstable volatile olefin complexes can be prepared by either using high pressures of olefin to stabilize copper$^{+1}$ and then effecting a CVD deposition by releasing the pressure or, using low temperatures and high olefin pressures to stabilize copper$^{+1}$ then effecting a copper deposition by warming and/or pressure drop.

The present process has the ability to selectively deposit copper films having small grain size at low temperatures, i.e., from 110° to 190° C., without significantly compromising the growth rate of the film. The small grain size of the deposited metal minimizes the need for post deposition planarization. Additionally, the ability to deposit copper at these lower temperatures is especially important for the so called upper-level metals in multi-metal layer ICs as excessive heat is to be avoided during the later stages of microprocessor fabrication to prevent thermally induced interdiffusion of of layer materials and dopants at device interfaces. Also, since useful deposition rates, appropriate grain size etc. can be accomplished below 200° C., standard photoresist materials can be used for patterning purposes via photolithographic techniques.

Additionally, the present process is advantageous in that it does not result in the release of corrosive or otherwise detrimental byproducts that can lead to a loss of selectivity or damage to the microprocessor substrate.

In an additional embodiment, hydrogen can be used in the CVD reduction of the organometallic copper complexes of the present invention, such as Cu$^{+1}$(hfac)-·olefin complexes, to yield metallic copper in a similar manner that it is reported to reduce Cu$^{+2}$(hfac)$_2$. This more effectively utilizes the precursor from the perspective that each metal center would yield metallic copper in contrast to the disproportionation reaction where only ½ of the initial Cu$^{+1}$ centers yield copper metal. In instances in which this results in the loss of selectivity, an initial selective deposition in the absence of hydrogen can be utilized to deposit a seed layer of copper which would then be grown by subsequent CVD processing by hydrogen reduction. Optionally, other reducing gases could also be used.

It has also been found that the present CVD reaction could be reversed such that copper metal deposited via a blanket deposition reaction could be removed, i.e., etched from the metallic surface area of a substrate. In accordance with this technique, a copper (+2) complex along with a suitable olefin, both in the vapor phase, are brought into contact with a substrate onto which excess copper has been deposited. The copper metal on the surface of the substrate is converted into a volatile copper (+1) complex and is evaporated away from the metal. The general chemical equation for this etching reaction is as follows:

$$Cu^* + Cu^{+2}(ligand)_2 + 2\ olefin \rightarrow 2Cu^{+1}(ligand)olefin$$

Prior to the present invention, known etching processes were inappropriate for copper since prior processes resulted in the generation of copper halides which are involatile and were left behind as surface contaminants.

EXPERIMENTAL

Synthesis

In the following examples, temperatures are set forth uncorrected in degrees celcius. Unless otherwise noted, all parts and percentages are by weight. 1,1,1,5,5,5-hexafluoro-2,4-pentanedione was purchased from Fairfield Chemical Company (P.O. Box 20, Blythewood, SC 29106). 1,5-cyclooctadiene (i.e. COD), norbornadiene (i.e. NB), potassium hydride, copper$^{+1}$ oxide and copper$^{+1}$ chloride were purchased from Aldrich Chemical Co. (940 H. St. Paul Avenue, Milwaukee Wis. 53233). HPLC grade terahydrofuran (THF) and hexane were individually distilled from sodium benzophenone under an atmosphere of nitrogen prior to use. All operations in the preparation of metal complexes were carried out using standard Schlenk line techniques as described by D. F. Shriver in the "Manipulations of Air Sensitive Compounds" McGraw-Hill Publishing Co. Copper$^{+1}$(hfac)·COD and {copper$^{+1}$(hfac)}$_2$·NB compounds, i.e. 1 and 2 respectively as shown in Table 1 were initially prepared by the method described by Doyle [Organometallics, Vol. 4, No. 5,830, (1985)]. This consisted of reacting cuprous oxide with one equivalent of hexafluoroacetylacetonate in THF solvent in the presence of one equivalent of olefin to yield the desired copper$^{+1}$ olefin complex and water, according to equation (1) shown below where the olefin is COD.

$$Cu_2O + 2H\text{-hfac} + 2COD \rightarrow 2Cu^{+1}(hfac)\cdot COD + H_2O \quad (1)$$

However, we found that while this synthesis yielded the desired complex, it was heavily contaminated with Cu$^{+2}$(hfac)$_2$. Although Doyle claims that these complexes are moisture insensitive we have found during the course of our research that this is not so and that the presence of water leads to some of the copper$^{+1}$olefin complex to decompose to copper$^{+2}$ complex and copper, presumably via a disproportionation machanism. This copper$^{+2}$ contaminant then has to be removed via a series of recrystallizations and sublimations. To overcome this problem we developed a new "water free" synthesis where the potassium salt of hfac is reacted with cuprous chloride in THF solvent in the presence of one equivalent of olefin. This yields the desired copper olefin complex and potassium chloride by-product as shown below in equation 2:

$$K^+hfac^- + CuCl + olefin \rightarrow Cu^{+1}(hfac)\cdot(olefin) + KCl \qquad (2)$$

No $Cu^{+2}(hfac)_2$ was observed to form. We believe that this represents a generic route to any $copper^{+1}$ ($\beta$-diketonate)·olefin complex. An example of this route is shown below for the synthesis of $copper^{+1}(hfac)\cdot COD$:

Under a blanket of dry nitrogen 0.80g ($2 \times 10^{-2}$ moles) of potassium hydride are charged into a 100 ml Schlenk flask fitted with a rubber septum. 25 ml of dry tetrahydrofuran (THF) solvent are then added to the hydride via canula, the nitrogen atmosphere vented and 2.82 ml (4.16 g $2 \times 10^{-2}$ moles) of hexafluoroacetylacetonate slowly added via syringe over a 10 minute period with stirring. A vigorous evolution of hydrogen is observed and stirring is continued until it ceases. A second nitrogen filled 100 ml Schlenk flask is charged with 1.98 g ($2 \times 10^{-2}$ moles) of cuprous chloride and 10 ml of dry THF solvent are added into the flask along with the 2.54 ml ($2 \times 10^{31\ 2}$ moles) of 1,5-cyclooctadiene. The initial potassium hexafluoroacetylacetonate solution is then added via canula into the second flask with stirring. A bright yellow coloration is observed. After two hours of stirring at room temperature the solution is filtered under nitrogen to yield a clear yellow solution. The THF is then evaporated to give an 80% yield of $copper^{+1}(hfac)\cdot COD$ as a bright yellow crystalline solid which can be further purified by recrystallization from dry hexane or sublimation at 65° C., $10^{-3}$ torr.

EXAMPLES 1-11

The selective metallizations of various substrates were performed using the apparatus shown in the accompanying FIGURE. Under an atmosphere of nitrogen the source chamber 1 was loaded with 0.5-1.5 g of volatile $copper^{+1}$ hexafluoroacetylacetonate·olefin complex and then fitted to the precursor feed tube 3. Valve 5 was then closed. The susceptor 7 was then fitted with two silicon coupons 8 & 9, side by side, one bearing a silicon oxide surface and the other a metallized surface (i.e. TiN, Ta etc.). Alternatively, just one coupon bearing a silicon oxide/metal patterned surface (e.g. a $W/SiO_2$ FLTC) was fitted to the susceptor. The entire susceptor assembly was then loaded into the deposition chamber 11 and a teflon stopper 12 was fitted in the top of the deposition chamber 11 through which a thermocouple 14 passes from the susceptor 7 to a temperature controller, and a heater rod 16 passes from the temperature controller to the suscepter 7. A condensor 13 was then connected to deposition chamber 11 with valve 15 closed. A vacuum line 17 and two cold water lines 19 & 21 were then connected to condensor 13. Valves 5 and 15 were then opened and the entire apparatus evacuated to 50 mtorr pressure. After a few minutes valve 5 is closed and the entire apparatus was lowered into a thermostated oil bath set at the desired source temperature up to the immersion line indicated. The thermostated heat for the susceptor was turned on and the susceptor allowed to reach the predetermined temperature (from 130°-180° C.). The apparatus was then left one hour or longer under vacuum (50 mtorr). The cooling water to the condensor was then turned on. After this time period valve 5 was opened thereby allowing vapors of the precursor to be drawn through the deposition chamber and to deposit a copper film on the susceptor and its mounted substrate(s). At the end of a run valve 5 was shut, the entire apparatus was backfilled with nitrogen gas and the susceptor assembly removed. $Cu^{+2}(hfac)_2$ was observed as sublimate collected onto the cold finger of the condensor along with unreacted $Cu^+hfac\cdot olefin$ complex.

In Example 10 a similar piece of equipment was utilized to show that compound 1 could be vaporized at 105° C. in a flow of dry nitrogen at one atmosphere pressure and the resultant vapor passed over a silicon coupon at 150° C. to yield a film of pure copper metal.

The results of these metallizations along with the specific complexes, substrates, and reaction conditions are listed in Table 1 below. Selectivity was determined by both visual inspection of the coupons at 200-1000 X using an optical microscope and by a scanning electron microscope (SEM) to determine the presence or absence of copper. The thickness of each deposited film was determined by viewing them edge on in SEM. The purity of the copper deposited was determined via Auger electron spectroscopy depth profiling. The purity of the copper films deposited onto TiN and Ta surfaces were measured from the metallized coupons used in runs 8 & 9 respectively. The purity of the copper film deposited onto tungsten was measured from the FLTC wafer used in run 2.

In all cases the purity of the copper was found to be >99.9% with carbon, oxygen, and fluoride being below detectable limits.

TABLE 1

| Run | Precursor* | Substrates | Source Temperature (Deposition Temp) (°C.) | Substrates Temperature (°C.) | Pressure (m torr) | Duration of Runs (mins) | Selectivity | Film Thickness (microns) | Average Grain Size | Approximate Deposition Rate |
|---|---|---|---|---|---|---|---|---|---|---|
| 1 | A | $W^1$ vs. $SiO_2^2$ | 100 | 130 | 300 | 3 | W | 0.1 | 0.2-0.3 m | 30 nm/min |
| 2 | A | $W^3$ vs. $SiO_2^3$ | 100 | 150 | 300 | 3 | W | 0.4 | 0.2-0.3 m | 130 nm/min |
| 3 | A | $W^1$ vs. $SiO_2^2$ | 100-105 | 180 | 500 | 25 | W | 0.5 | 0.5-1.0 m | 20 nm/min |
| 4 | A | $W^3$ vs. $SiO_2^3$ | 106 | 150 | 20 | 12 | W | 2.0 | 0.5 m | 160 nm/min |
| 5 | A | $W^3$ vs. $SiO_2^3$ | 107 | 200 | 50 | 15 | Blanket | 1.5 | 0.2 m | 100 nm/min |
| 6 | B | $W^3$ vs. $SiO_2^3$ | 112 | 150 | 10 | 37 | W | 0.2 | 0.1 m | 5 nm/min |
| 7 | B | $W^3$ vs. $SiO_2^3$ | 145 | 150 | 50 | 4 | N | 0.7 | 0.3 m | 175 nm/min |
| 8 | A | $TiN^4$ vs. $SiO_3^2$ | 115 | 150 | 50 | 4 | TiN | 0.05 | 0.2-0.3 m | 10 nm/min |
| 9 | A | $Ta^5$ vs. $SiO_2^2$ | 112 | 150 | 50 | 4 | Ta | 0.1 | 0.1-0.3 m | 25 nm/min |
| 10 | A | $Si^6$ alone | 105 | 150 | 1 atm ($N_2$) | 30 | Si | >0.1 | 0.4 m | >3 nm/min |

TABLE 1-continued

| Run | Pre-cursor* | Substrates | Source Temperature (Deposition Temp) (°C.) | Substrates Temperature (°C.) | Pressure (m torr) | Duration of Runs (mins) | Select-ivity | Film Thickness (microns) | Average Grain Size | Approximate Deposition Rate |
|---|---|---|---|---|---|---|---|---|---|---|
| 11 | A | W³ vs. SiO₂³ | 100 | 100 | 50 | 20 | NO DEPOSITION OBSERVED | | | |

*A = copper⁺¹(hfac).COD
B = [copper⁺¹(hfac)]₂.norbornadiene
¹Tungsten deposited onto silicon from tungsten hexafluoride
²Silicon oxide deposited onto Si from tetraethoxysilane (TEOS)
³FLTC - tungsten vs. silicon oxide patterned wafer
⁴Silicon (100) wafer onto which a 550 · TiN layer was deposited by Reaction ion sputtering.
⁵Silicon wafer onto which 500 · of SiO₂ were thermally grown then 1200 · of tantalum metal reactive ion was sputtered onto the silicon oxide.
⁶Silicon (100) wafer

EXAMPLE 12

A run was carried out to demonstrate the ability to etch excess copper from the surface of a substrate. This process was demonstrated using Cu⁺²(hfac)₂ along with 1-tridecene as the olefin since the volatilities of both are comparable. 1.0 g of Cu⁺²(hfac)₂ was added to 3 ml of 1-tridecene and the mixture heated to 60° C. then cooled to room temperature. Some copper complex precipitated out and was discarded. The saturated solution of complex in 1-tridecene was then heated to 120° C. and 200 ml/min of nitrogen bubbled through it to produce a nitrogen/complex/olefin vapor mixture. This vapor was then passed over a copper covered surface heated to 120° C. for one hour, resulting in an etching of the copper surface. The etched sample was a silicon coupon that had been covered sequentially with 5000 Å of silicon oxide, 1200 Å of tantalum and 1000 Å of copper. The surface of the coupon was partially masked with polyimide tape such that only a narrow trench of copper was exposed to the etch vapors. Once the etch was completed, the tape was removed and the extent of the etch determined by measuring the depth of copper removed from the surface via a stylus profilometer. In this technique, a sapphire stylus point contacts and tracks across the surface of the etched coupon and directly measures its surface topography in units of Angstroms. In addition, the etched surface was also examined by a scanning electron microscope. Both of these techniques confirmed that copper had been etched right down to the tantalum underlayment.

Having thus described the present invention, what is now deemed appropriate for Letters Patent is set out in the following appended claims.

We claim:

1. In a process for the chemical vapor deposition of a copper metal film onto a substrate wherein at least a portion of the surface of said substrate is metallic or other electrically conducting material, by contacting said substrate with a volatile organometallic copper precursor in the gas phase, the improvement for selectively depositing said copper film on the metallic or other electrically conducting portion of the surface of the substrate, at a deposition temperature from 110° to 190° C. which comprises:

using as said volatile organometallic copper precursor a complex having a vapor pressure greater than or equal to 0.01 mm Hg at 100° C. represented by the structural formula:

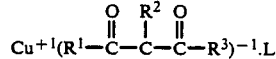

where R¹ and R³ are each independently C₁-C₈ perfluoroalkyl, R² is H or C₁-C₈ perfluoroalkyl and L is carbon monoxide, an isonitrile, or an unsaturated hydrocarbon ligand containing at least one non-aromatic unsaturation.

2. The process of claim 1 wherein R² is H.

3. The process of claim 1 wherein the volatile copper organic precursor is Cu⁺¹(hexafluoroacetylacetonate⁻¹)·1,5-cyclooctadiene.

4. The process of claim 1 wherein the volatile copper organic precursor is {Cu⁺¹(hexafluoroacetylacetonate⁻¹)}₂·norbornadiene.

5. The process of claim 1 wherein the deposition temperature is from 130° to 180° C.

6. The process of claim 1 wherein the surface onto which the copper metal film is deposited is selected from the group consisting of: W, TiN, Ta, and Al.

7. The process of claim 1 wherein said substrate is contacted with hydrogen gas along with the organometallic precursor.

8. A process for selectively etching a copper film from the surface of a substrate, said process comprising:
contacting the substrate having a copper film surface with an organometallic copper complex and a ligand, both in the gas phase and at a temperature from 110° to 190° C., wherein said complex and said ligand are represented by the structural formulae:

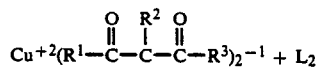

where R¹ and R³ are each independently C₁-C₈ perfluoroalkyl, R² is H or C₁-C₈ perfluoroalkyl and L is carbon monoxide, an isonitrile, or an unsaturated hydrocarbon containing at least one non-aromatic unsaturation.

9. The process of claim 8 wherein R² is H.

10. The process of claim 8 wherein L is an olefin.

11. The process of claim 10 wherein the organometallic copper complex is Cu⁺²(hexafluoroacetylacetonate⁻¹)₂ and the olefin is 1-tridecene.

12. The process of claim 8 wherein said substrate is contacted with the organometallic copper complex at a temperature from 130° to 180° C.

* * * * *